United States Patent [19]

Walker et al.

[11] 4,036,975
[45] July 19, 1977

[54] 1-[2-(1-ADAMANTYL)-2-(R-THIO)ETHYL-]IMIDAZOLES AND 1-[2-(1-ADAMANTYL)-2-(R-OXY)ETHYL-]IMIDAZOLES

[75] Inventors: Keith A. M. Walker, Palo Alto; Stefan Howard Unger, Cupertino, both of Calif.

[73] Assignee: Xyntex (U.S.A.) Inc., Palo Alto, Calif.

[21] Appl. No.: 665,012

[22] Filed: Mar. 8, 1976

Related U.S. Application Data

[63] Continuation-in-part of Ser. No. 599,441, July 28, 1975, abandoned.

[51] Int. Cl.² .................. A61K 31/415; C07D 233/60
[52] U.S. Cl. ..................................... 424/273; 260/309; 260/586 G; 260/609 F
[58] Field of Search ........................ 260/309; 424/273

[56] References Cited

U.S. PATENT DOCUMENTS 3,682,951  8/1970  Kreider .................................. 260/309

*Primary Examiner*—Natalie Trousof
*Attorney, Agent, or Firm*—Alan M. Krubiner; William B. Walker

[57] ABSTRACT

Compounds of the formula

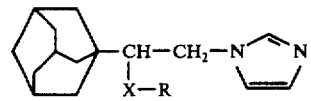

(I)

wherein R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl; and X is oxygen or sulfur with the proviso that X is not oxygen when R is phenyl or substituted phenyl; and the antimicrobial acid addition salts thereof are useful as antifungal, antibacterial and antiprotozoal agents.

28 Claims, No Drawings

1-[2-(1-ADAMANTYL)-2-(R-THIO)ETHYL-]IMIDAZOLES AND 1-[2-(1-ADAMANTYL)-2-(R-OXY)ETHYL-]IMIDAZOLES

RELATED APPLICATIONS

This case is a continuation-in-part of U.S. Ser. No. 599,441, filed July 28, 1974, now abandoned.

The present invention relates to certain substituted N-adamantylethylimidazole derivatives. More particularly, the present invention relates to compounds having the formula

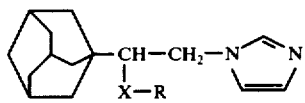

and the antimicrobial acid addition salts thereof, wherein:

R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl; and X is oxygen or sulfur with the proviso that X is not oxygen when R is phenyl or substituted phenyl.

The term "alkyl" as used in the specification and appended claims refers to a straight or branched chain monovalent substituent consisting solely of carbon and hydrogen, containing no unsaturation, and having from one to 12 carbon atoms. Examples of alkyl groups are methyl, ethyl, n-propyl, i-propyl, n-butyl, sec-butyl, t-butyl, n-pentyl, n-hexyl, n-octyl, n-nonyl, n-decyl, n-dodecyl and the like. The term "lower alkyl" refers to an alkyl group as previously defined having 1 to 4 carbon atoms. The term "cycloalkyl" refers to a monocyclic, monovalent substituent consisting solely of carbon and hydrogen, containing no unsaturation, and having 5 to 7 carbon atoms. Examples of cycloalkyl groups are cyclopentyl, cyclohexyl, and cycloheptyl. The term "cycloalkyl lower alkyl" refers to a cycloalkyl group as previously defined attached to a straight chain lower alkyl group as previously defined. Examples of cycloalkyl lower alkyl groups are cyclopentylpropyl, cyclohexylmethyl, cyclohexylethyl and the like. The term "phenyl lower alkyl" as used herein refers to a phenyl group attached to a straight chain lower alkyl group as previously defined. Examples of phenyl lower alkyl groups are benzyl, phenethyl and 3-phenylpropyl. The term "halo" refers to fluoro, chloro and bromo. The term "antimicrobial acid addition salts" refers to salts of the subject compounds which possess the desired activity and which are neither biologically nor otherwise undesirable. These salts are formed with inorganic acids such as hydrochloric acid, hydrobromic acid, sulfuric acid, nitric acid and phosphoric acid, or organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluene sulfonic acid and the like.

All compounds of Formula (I) possess at least one chiral center, i.e., the carbon atom to which are attached the

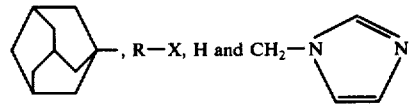

moieties. Accordingly, the compounds of the present invention may be prepared in either optically active form, or as a racemic mixture. Unless otherwise specified, the compounds described herein are all in the racemic form. However, the scope of the subject invention herein is not be considered limited to the racemic form, but to encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of Formula (I) or the alcohol precursors of compounds of Formula (I) in which X is oxygen, with an optically active acid, or by separation of the diastereomeric esters formed by reaction of racemic alcohol precursors of compounds of Formula (I) with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid and the like. The separated pure diastereomeric salts or esters may then be cleaved by standard means to afford the respective optical isomers of the compounds of Formula (I) or the precursor alcohols.

The subject compounds of Formula (I) and the antimicrobial acid addition salts thereof can be represented more specifically by the following subgeneric formulas:

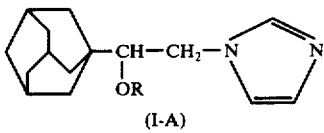

(I-A)

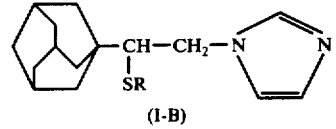

(I-B)

wherein:

R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl with the proviso that R cannot be phenyl or substituted phenyl in compounds of Formula (I-A).

Preferred compounds embraced by the above subgeneric Formulas (I-A) and (I-B) are those wherein R is alkyl, halo substituted benzyl or halo substituted phenyl.

Particularly preferred compounds within the group described in the previous paragraph are those wherein R is a straight chain alkyl, 4-halo substituted benzyl, 4-halo substituted phenyl, 2,4-di-, or 3,4-dichloro substituted benzyl or 2,4-di- or 3,4-dichloro substituted phenyl. Most particularly preferred compounds within the 4-halo substituted benzyl and 4-halo substituted phenyl series are those where R is 4-chlorobenzyl or R is 4-chlorophenyl.

The subject compounds are Formula (I) exhibit antifungal, anti-bacterial and anti-protozoal activity. For example, compounds of the present invention exhibit anti-fungal activity against human and animal pathogens such as

*Microsporum audouini,*
*Microsporum gypseum,*
*Microsporum gypseum — canis,*
*Epidermophyton fluoccosum*
*Trichophyton mentagrophytes,*
*Trichophytrum,*
*Trichophyton tonsurans,*
*Candida albicans, and*
*Cryptococcus neoformans.*

The compounds of the present invention also exhibit anti-fungal activity against organisms primarily of agricultural importance, such as

*Aspergillus flavus,*
*Cladosporium herbarum,*
*Fusarium graminearum,*
*Penicillium notatum,*
*Aspergillus niger,*
*Penicillium oxalicum,*
*Penicillium spinulosum, and*
*Pithomyces chartarum.*

In addition, the compounds of the present invention exhibit anti-bacterial activity against human and animal pathogens, such as

*Staphylococcus aureus,*
*Streptococcus faecalis,*
*Corynebacterium acnes,*
*Erysipelothrix insidiosa,*
*Escherichia coli,*
*Proteus vulgaris,*
*Salmonella choleraesuis,*
*Pasteurella multocida, and*
*Pseudomonas aeruginosa.*

Moreover, the compounds of the present invention exhibit anti-protozoal activity against protozoa such as Trichomonas vaginalis.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of Formula (I) in combination with a suitable carrier. A Still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semisolid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous injection. Intravenous injection of imidazole derivatives for certain systemic conditions has been demonstrated to be effective (see for example, Drugs, 8, 419–420(1975), which describes the intravenous administration of Miconazole, i.e., 1-[2,4-dichloro-β-(2', 4'-dichlorobenzyloxy)phenethyl]imidazole nitrate, to patients with systemic candidiasis).

Topical application is the preferred method of administration in pharmaceutical applications. For such treatment, an area having an existing fungal, bacterial or protozoal growth, or to be protected against attack by fungi, bacteria or protozoa may be treated with the subject compounds or compositions by, for example, dusting, sprinkling, spraying, rinsing, brushing, dipping, smearing, coating, impregnating and the like. Topical compositions containing the compounds of the present invention exhibit anti-fungal, anti-bacterial and anti-protozoal activity over a wide range of concentration, for example, from about 0.1 to 10.0% by weight of the composition.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g. oral or parenteral) administration it is expedient to administer the active ingredient in amounts of between about 1 and 100 mg./kg. body weight per day (preferably between about 5 and 50 mg./kg. body weight per day) distributed over several applications (e.g. in 3 individual doses) in order to achieve effective results. For localized (e.g. topical) administration however, proportionately less of the active ingredient is required. The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner. In any event, the compositions to be administered will contain a quantity of the subject compound in an amount effective for relief or prevention of the specific condition being treated.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known matter. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

DETAILED DESCRIPTION

The present invention, in a still further aspect, is directed to methods for the preparation of the subject compounds of Formula (I).

The following reaction sequence is directed to the preparation of compounds of Formula (I-A).

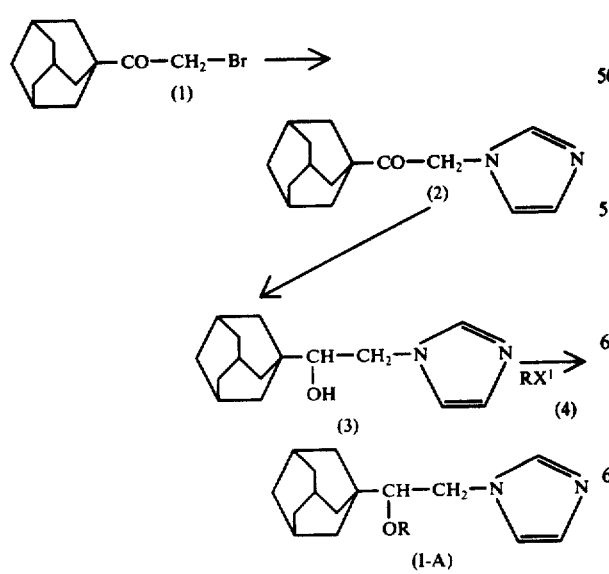

wherein R is as previously defined and subject to the previous proviso, i.e., R cannot be phenyl or substituted phenyl, and $X^1$ is chloro, bromo, iodo or a reactive ester group such as $CH_3S(O)_2$—O— or p—$CH_3$—$C_6H_4$—S-$(O)_2O$—.

1-Adamantyl-1-imidazolylmethyl ketone of Formula (2) is prepared by treating 1-adamantyl bromomethyl ketone of Formula (1) with imidazole in an organic solvent such as acetonitrile, dimethylformamide and the like at a temperature of 0° to 25° C. for a period of 12 hours.

The thus obtained 1-adamantyl-1-imidazolylmethyl ketone of Formula (2) is then reduced with a complex metal hydride such as sodium borohydride to obtain 1-[2-(1-adamantyl)-2-hydroxyethyl]imidazole of Formula (3). The reduction is carried out in an inert organic solvent such as methanol at a temperature of 0° to 25° C.

The 1-[2-(1-adamantyl)-2-(R-oxy)ethyl]imidazoles of Formula (I-A) are then prepared by first treating 1-[2-(1-adamantyl)-2-hydroxyethyl]imidazole (3) with a suitable base, such as sodium hydride and thereafter condensing the resulting salt with a compound of Formula (4), i.e., $RX^1$ wherein R is alkyl, cycloalkyl, cycloalkyl lower alkyl, phenyl lower alkyl or substituted phenyl lower alkyl and $X^1$ is chloro, bromo, iodo or a reactive ester group such as $CH_3$—$S(O)_2$—O— or p—$CH_3$-—$C_6H_4$—$S(O)_2$—O—.

The following reaction sequence is directed to the preparation of compounds of Formula (I-B):

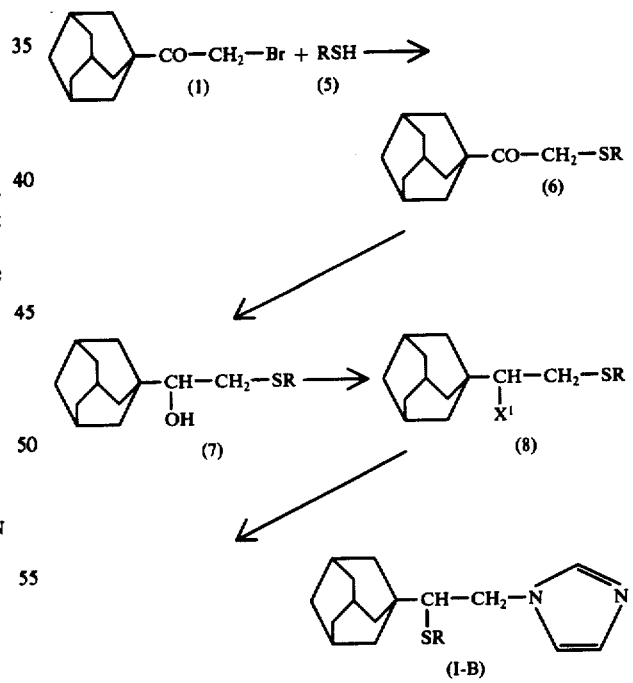

wherein R is as previously defined and $X^1$ represents a conventional leaving group such as halide (e.g., chloride or bromide) or a sulfonate ester (e.g. methanesulfonate or p-toluenesulfonate).

The 1-adamantyl R-thiomethyl ketones of Formula (6) are prepared by treating 1-adamantyl bromomethyl ketone (1) with a mercaptan or thiophenol of Formula (5).

The reaction of (1) with a mercaptan, i.e., a compound of Formula (5) wherein R in Formula (5) is alkyl, cycloalkyl, cycloalkyl lower alkykl, phenyl lower alkyl or substituted phenyl lower alkyl, is carried out in an inert organic solvent such as tetrahydrofuran and in the presence of sodium hydride or other suitable base at a temperature of 20° to 66° C. for a period of 30 minutes to 24 hours.

The reaction of (1) with a thiophenol, i.e., a compound of Formula (5) wherein R in Formula (5) is phenyl or substituted phenyl, is carried out in the presence of an inert organic solvent, e.g. acetone, methanol and the like, in the presence of potassium carbonate or other suitable base under reflux conditions for a period of 30 minutes to 12 hours.

The thus obtained 1-adamantyl R-thiomethyl ketones of Formula (6) are then reduced with an alkali metal borohydride such as sodium borohydride to obtain the 1-(1-adamantyl)-2-(R-thio) ethanols of Formula (7). The reduction is carried out in an inert organic solvent such as methanol, or ethanol at a temperature of 0° to 25° C. for a period of 10 minutes to 3 hours.

The 1-[2-(1-adamantyl)-2-(R-thio)ethyl]imidazoles of Formula (I-B) are prepared from compounds of Formula (7) by a two-step sequence involving conversion of the hydroxy group to a suitable leaving group such as a halide (e.g., a chloride or bromide) or a sulfonate ester (e.g., methanesulfonate or p-toluenesulfonate) followed by reaction with imidazole.

The conversion of an alcohol of formula (7) to a halide or sulfonate ester of Formula (8) is carried out by means well known in the art. For example, the alcohol may be halogenated using a halogenating agent such as thionyl chloride or thionyl bromide, either neat, or in an inert organic solvent such as dichloromethane or chloroform, at a temperature between about 0° to 80° C., preferably between about 20° and 80° C. The halogenation reaction may be carried out in the presence of a molar equivalent of a base (e.g., pyridine) if desired. Alternate halogenation procedures include, for example, the use of triphenylphosphine with ether carbon tetrachloride, carbon tetrabromide, or N-chloro (or N-bromo) succinimide.

Sulfonate esters may be prepared by the standard procedure of treating the alcohol with an excess of, for example, methanesulfonyl chloride or p-toluenesulfonyl chloride, in the presence of a base, for example pyridine or triethylamine. This reaction is carried out at a temperature from about −20° to +50° C., preferably between about 0° and 20° C.

The halides or sulfonate esters of Formula (8) are then treated with imidazole in an organic solvent with as acetonitrile, dimethylformamide and the like at a temperature of 0° to 100° C. for a period of 1 to 24 hours to obtain the 1-[2-(1-adamantyl)-2-(R-thio)ethyl]imidazoles of Formula (I-B).

The subject compounds of the instant invention can be isolated as free bases, however, since many of the compounds in base form are oils or gums, it is more convenient to isolate and characterize the compounds as acid addition salts. These salts are prepared in the usual manner, i.e., by reaction of the base compound with suitable inorganic or organic acid, described above. Salts formed with dibasic acids (e.g. oxalic acid) may contain one or two molecules of base per molecule of acid. All oxalates described herein contain one molecule of oxalic acid per molecule of imidazole base. If desired, the salts can be readily converted to the compounds in base form by treatment with alkali, such as potassium carbonate, sodium carbonate or sodium or potassium hydroxide.

DESCRIPTION OF SPECIFIC EMBODIMENTS

The following specific description is given to enable those skilled in the art to more clearly understand and practice the present invention. It should not be considered a limitation upon the scope of the invention but merely as being illustrative and representative thereof.

EXAMPLE 1

1-adamantyl 1-imidazolylmethyl ketone

A solution of 5 g. of 1-adamantyl bromomethyl ketone in 10 ml. of dimethylformamide is added dropwise with stirring and ice-cooling to 7 g. imidazole in 10 ml. dimethylformamide. The resulting solution is stirred overnight at room temperature and then poured into 250 ml. water. The precipitate which forms is filtered off, washed with water and air dried. Thereafter the resulting residue is chromatographed on silica gel to effect purification. Elution with 10% acetone in dichloromethane yields 1-adamantyl 1-imidazolylmethyl ketone, M.P. 128.5°-129.5° C.

EXAMPLE 2

1-[2-(1-adamantyl)-2-hydroxyethyl]imidazole

A solution of 3.05 g. of 1-adamantyl 1-imidazolylmethyl ketone in 40 ml. methanol is treated at 0° to 5° C. with excess sodium borohydride. When reduction is complete, the solvent is removed and 100 ml. of water is added to the residue. The product is filtered off and recrystallized from ethyl acetate to yield 1-[2-(1-adamantyl)-2-hydroxyethyl]imidazole, M.P. 226°-227.5° C.

EXAMPLE 3

1-[2-(1-adamantyl)-2-(2,4-dichlorobenzyloxy)ethyl]imidazole

To a solution of 500 mg. of 1-[2-(1-adamantyl)-2-hydroxyethyl]imidazole in 3 ml. of hexamethylphosphoramide is added 96 mg. of a 56% dispersion of sodium hydride in mineral oil. The addition of base is carried out under a nitrogen atmosphere with continuous stirring. The reaction temperature is then maintained at 25° C. for 1 hour and thereafter at 50° C. After 1½ hours at 50° C., the reaction mixture is cooled in ice and 450 mg. α,2,4-trichlorotoluene in 3 ml. hexamethylphosphoramide is added dropwise. The temperature is then held at 5° C. for a 1 hour, then raised to 25° C. for 1 hour, and finally held at 50° C. for 2 hours. Thereafter, the resulting solution is poured into 200 ml. water. The aqueous phase is extracted with ether and the extracts washed with water, dried over magnesium sulfate and evaporated to dryness. The resulting residue is chromatographed on silica gel to effect purification. Elution with 5% acetone in dichloromethane yields 1-[2-(1-adamantyl)-2-(2,4-dichlorobenzyloxy)ethyl]imidazole which is then further characterized as the oxalate salt, decomp. 203.5°-205.5° C.

Similarly, substituting other compounds of formula (4) for α,2,4-trichlorotoluene, for example,
  methyl iodide,
  n-hexyl bromide,
  n-dodecyl chloride,
  cyclopentyl chloride, cyclohexylmethyl bromide,
benzyl chloride,
4-t-butylbenzyl chloride,
4-bromobenzyl chloride,
4-chlorobenzyl chloride and
3,4-dichlorobenzyl chloride
is productive of the following 1-[2-(1-adamantyl)-2-(R-oxy)ethyl]imidazoles:

1-[2-(1-adamantyl)-2-(methoxy)ethyl]imidazole,
1-[2-(1-adamantyl)-2-(n-hexyloxy)ethyl]imidazole,
1-[2-(1-adamantyl)-2-(n-dodecyloxy)ethyl]imidazole,
1-[2-(1-adamantyl)-2-(cyclopentyloxy)ethyl]imidazole,
1-[2-(1-adamantyl)-2-cyclohexylmethoxy)ethyl]imidazole,
1-[2-(1-adamantyl)-2-(benzyloxy)ethyl]imidazole,
1-[2-(1-adamantyl)-2-(4-t-butylbenzyloxy)-ethyl]imidazole,
1-[2-(1-adamantyl)-2-(4-bromobenzyloxy)ethyl]imidazole,
1-[2-(1-adamantyl)-2-(4-chlorobenzyloxy)ethyl]imidazole, and
1-[2-(1-adamantyl)-2-(3,4-dichlorobenzyloxy)ethyl]imidazole.

EXAMPLE 4

1-adamantyl-4-chlorobenzylthiomethyl ketone

A 56% dispersion of sodium hydride in mineral oil (300 mg.) is added with stirring to 1.3 g. 4-chlorobenzyl mercaptan in 40 ml. of tetrahydrofuran. To the resulting salt suspension is added 1.3 g. of 1-adamantyl bromomethyl ketone in 10 ml. of tetrahydrofuran. After stirring for 1 hour at room temperature the solvent is removed, 100 ml. of ether is added and the mixture is then washed with water and dried over magnesium sulfate. The solvent is then removed to yield 1-adamantyl-4-chlorobenzylthiomethyl ketone which is used without further purification in the following Example.

EXAMPLE 5

1-(1-adamantyl)-2-(4-chlorobenzylthio)ethanol 1-adamantyl-4-chlorobenzylthiomethyl ketone, obtained in Example 4, in 250 ml. of methanol is treated at 0°-5° C. with excess sodium borohydride until reduction is complete. The solvent is then removed, 50 ml. of water is added and the product is extracted with ether. The combined extracts are washed with water, dried over magnesium sulfate and evaporated to dryness. Recrystallization of the product from hexane yields 1-(1-adamantyl)-2-(4-chlorobenzylthio)ethanol, M.P. 74°-79° C.

EXAMPLE 6

1-[2-(1-adamantyl)-2-(4-chlorobenzylthio)ethyl]imidazole

To a solution of 1-(1-adamantyl)-2-(4-chlorobenzylthion)ethanol (400 mg.) in 10 ml. of dichloromethane is added 1 ml. of thionyl chloride. After 1 hour at room temperature the reaction mixture is evaporated to dryness. The residue is then added to 1 g. of imidazole and 5 ml. of acetonitrile and stirring is maintained overnight at room temperature. Thereafter, the solvent is removed, 50 ml. of water is added and the mixture is extracted with ether. The ether extracts are washed with water and dried over magnesium sulfate to obtain 1-[2-(1-adamantyl)-2-(4-chlorobenzylthio)ethyl]imidazole which is then further characterized as the nitrate salt, M.P. 157°-160° C. (with foaming).

EXAMPLE 7

Repeating the procedures of Examples 4-6, but replacing 4-chlorobenzyl mercaptan in Example 4 with other compounds of formula (5), for example
ethyl mercaptan,
n-heptyl mercaptan,
n-dodecyl mercaptan,
cyclohexyl mercaptan,
cyclohexylmethyl mercaptan,
benzyl mercaptan,
4-methylbenzyl mercaptan,
2,4-dichlorobenzyl mercaptan, and
3,4-dichlorobenzyl mercaptan
is productive of the following 1-[2-(1-adamantyl)-2-(R-thio)ethyl]imidazoles which, where indicated, are further characterized by conversion in the usual manner to the indicated acid addition salt:

1-[2-(1-adamantyl)-2-(ethylthio)ethyl]imidazole, maleate salt, m.p. 146°-146.5° C. (foaming),
1-2-(1-adamantyl)-2-(n-heptylthio)ethyl]imidazole, oxalate salt, m.p. 204°-205.5° C. (foaming),
1-[2-(1-adamantyl)-2-(n-dodecylthio)ethyl]imidazole, hydrochloride salt, m.p. 207°-216° C, coalesces 207° C.,
1-2-(1-adamantyl)-2-(cyclohexylthio)ethyl]imidazole,
1-[2-(1-adamantyl)-2-(cyclohexylmethylthio)ethyl]imidazole,
1-[2-(1-adamantyl)-2-(benzylthio)ethyl]imidazole, hydrobromide salt, decomp. 228°-230° C.,
1[2-(1-adamantyl)-2-(4-methylbenzylthio)ethyl[imidazole, hydrobromide salt, decomp. 221°-221.5° C.,
1-[2-(1-adamantyl)-2-(2,4-dichlorobenzylthio)ethyl]imidazole, oxalate salt, and
1-2-(1-adamantyl)-2-(3,4-dichlorobenzylthio)ethyl]imidazole, oxalate salt.

EXAMPLE 8

1-adamantyl 3,4 dichlorophenylthiomethyl ketone 1-adamantyl bromomethyl ketone (1.3 g.), 1.1 g. of 3,4-dichlorothiophenol and 800 mg. of anhydrous potassium carbonate in 30 ml. of acetone are stirred at reflux overnight. The solvent is then removed and 60 ml. of water is added to the reaction mixture. The product is filtered off, washed with water and recrystallized from methanol to yield 1-adamantyl 3,4-dichlorophenylthiomethyl ketone, M.P. 105°-110.5° C.

EXAMPLE 9

1-(1-adamantyl)-2-(3,4-dichlorophenylthio)ethanol 1-adamantyl 3,4-dichlorophenylthiomethyl ketone (1.2 g.) in 250 ml. of methanol is treated with excess sodium borohydride with stirring and ice cooling. When reduction is complete, the solvent is removed, 50 ml. of water is added and the product is extracted with ether. The combined extracts are washed with water, dried over magnesium sulfate and evaporated to dryness to yield 1-(1-adamantyl)-2-(3,4-dichlorophenylthio)ethanol.

EXAMPLE 10

1-2-(1-adamantyl)-2-(3,4-dichlorophenylthio)ethyl-]imidazole

To 1.2 g. of 1-(1-adamantyl)-2-(3,4-dichlorophenylthio)ethanol in 40 ml. dichloromethane is added 1 ml. of thionyl chloride and the solution is then warmed at gentle reflux. After 30 minutes, the solution is evaporated to dryness and 2 g. of imidazole and 13 ml. acetonitrile is added to the residue. The mixture is stirred and heated overnight at 60° C. The solvent is then removed 50 ml. of water is added to the residue and the mixture is extracted with ether. The combined extracts are washed with water and dried over magnesium sulfate to yield 1-[2-(1-adamantyl)-2-(3,4-dichlorophenylthio)ethyl]imidazole which is then further characterized as the nitrate salt, M.P. 179°-181° C. (with foaming).

EXAMPLE 11

Repeating the procedures of Examples 8-10, but replacing 3,4-dichlorothiophenol in Example 8 with other compounds of formula (5), for example
thiophenol,
3-methylthiophenol,
4-t-butylthiophenol,
4-t-butyl-2-methylthiophenol,
3-bromo-4-methylthiophenol,
4-chloro-3-trifluoromethylthiophenol,
4-fluorothiophenol,
4-chlorothiophenol,
2,4-dichlorothiophenol
2,4,5-trichlorothiopenol,
3,4,5-trichlorothiophenol,
pentachlorothiophenol, and
4-trifluoromethylthiophenol is productive of the following 1-[2-(1-adamantyl)-2-(phenylthio)ethyl-]imidazoles which, where indicated, are further characterized by conversion to the indicated acid addition salt by treatment in the usual manner:
1-[2-(1-adamantyl)-2-(phenylthio)ethyl]imidazole,
1-[2-(1-adamantyl)-2-(3-methylphenylthio)ethyl-]imidazole,
1-[2-(1-adamantyl)-2-(4-t-butylphenylthio)ethyl-]imidazole, nitrate salt, m.p. 175°-178° C. (foaming),
1-[2-(1-adamantyl)-2-(4-t-butyl-2-methylphenylthio)ethyl]imidazole,
1-[2-(1-adamantyl)-2-(3-bromo-4-methylphenylthio)ethyl]imidazole,
1-[2-(1-adamantyl)-2-(4-chloro-3-trifluoromethylphenylthio)ethyl]imidazole,
1-[2-(1-adamantyl)-2-(4-fluorophenylthio)ethyl-]imidazole,
1-[2-(1-adamantyl)-2-(4-chlorophenylthio)ethyl-]imidazole,
1-[2-(1-adamantyl)-2-(2,4-dichlorophenylthio)ethyl-]imidazole,
1-[2-(1-adamantyl)-2-(2,4,5-trichlorophenylthio)ethyl]imidazole,
1-[2-(1-adamantyl)-2-(3,4,5-trichlorophenylthio)ethyl]imidazole,
1-[2-(1-adamantyl)-2-(pentachlorophenylthio)ethyl-]imidazole, and
1-[2-(1-adamantyl)-2-(4-trifluoromethylphenylthio)ethyl]imidazole.

EXAMPLE 12

Repeating the procedures of Examples 1-3, using reactants of formula (4) as dictated by the particular 1-[2-(1-adamantyl)-2-(R-oxy)-ethyl]imidazole desired, is productive of the following:
1-[2-(1-adamantyl)-2-(ethoxy)ethyl]imidazole,
1-[2-(1-adamantyl)-2-(n-propoxy)ethyl]imidazole,
1-[2-(1-adamantyl)-2-isopropoxy)ethyl]imidazole,
1-[2-(1-adamantyl)-2-(n-butoxy)ethyl]imidazole,
1-[2-(1-adamantyl)-2-(n-pentyloxy)ethyl]imidazole,
1-[2-(1-adamantyl)-2-(n-heptyloxy)ethyl]imidazole,
1-[2-(1-adamantyl)-2-(n-octyloxy)ethyl]imidazole,
1-[2-(1-adamantyl)-2-(cyclohexyloxy)ethyl-]imidazole,
1-[2-(1-adamantyl)-2-(cycloheptyloxy)ethyl-]imidazole,
1-[2-(1-adamantyl)-2-(3-cyclopentylpropoxy)ethyl-]imidazole,
1-[2-(1-adamantyl)-2-(cyclohexylethoxy)ethyl-]imidazole,
1-[2-(1-adamantyl)-2-(2-phenylethoxy)ethyl-]imidazole,
1-[2-(1-adamantyl)-2-(3-phenylpropoxy)ethyl-]imidazole,
1-[2-(1-adamantyl)-2-(4-methylbenzyloxy)ethyl-]imidazole,
1-[2-(1-adamantyl)-2-(3-(3-methylphenyl)propoxy)ethyl]imidazole,
1-[2-(1-adamantyl)-2-(4-trifluorobenzyloxy)ethyl-]imidazole,
1-[2-(1-adamantyl)-2-(4-fluorobenzyloxy)ethyl-]imidazole, and
1[2-(1-adamantyl)-2-(3-(4-chlorophenyl)propoxy)ethyl]imidazole.

EXAMPLE 13

Repeating the procedures of Examples 4-6, using reactants of formula (5) as dictated by the particular 1-[2-(1-adamantyl)-2-(R-thio)ethyl]imidazole desired, is productive of the following:
1-[2-(1-adamantyl)-2-(methylthio)ethyl]imidazole,
1[2-(1-adamantyl)-2-(n-propylthio)ethyl]imidazole,
1-[2-(1-adamantyl)-2-(isopropylthio)ethyl]imidazole,
1-[2-(1-adamantyl)-2-(n-butylthio)ethyl]imidazole,
1-[2-(1-adamantyl)-2-(n-pentylthio)ethyl]imidazole,
1-[2-(1-adamantyl)-2-(n-hexylthio)ethyl]imidazole,
1-[2-(1-adamantyl)-2-(n-octylthio)ethyl]imidazole,
1-[2-(1-adamantyl)-2-(n-nonylthio)ethyl]imidazole,
1[2-(1-adamantyl)-2-(cyclopentylthio)ethyl-]imidazole,
1-[2-(1-adamantyl)-2-(cycloheptylthio)ethyl-]imidazole,
1-[2-(1-adamantyl)-2-(3-cyclopentylpropylthio)ethyl-]imidazole,
1-[2-(1-adamantyl)-2-(cycloheptylmethylthio)ethyl-]imidazole,
1-[2-(1-adamantyl)-2-)phenylethylthio)ethyl-]imidazole,
1-[2-(1-adamantyl)-2-(3-phenylpropylthio)ethyl-]imidazole,
1-[2-(1-adamantyl)-2-(3-phenylpropylthio)ethyl-]imidazole,
1-[2-(1-adamantyl)-2-(3-(4-methylphenyl)propylthio)ethyl]imidazole,
1-[2-(1-adamantyl)-2-(4-t-butylbenzylthio)ethyl-]imidazole, 1-[2-(1-adamantyl)-2-(3-(4-chlorophenyl)propylthio)ethyl]imidazole, 1-[2-(1-adamantyl)-2-(4-fluorobenzylthio)ethyl]imidazole, and 1-[2-(1-adamantyl)-2-(4-trifluoromethylbenzylthio)ethyl]imidazole.

EXAMPLE 14

A solution of 200 g. of 1-[2-(1-adamantyl)-2-(2,4-dichlorobenzyloxy)ethyl]imidazole in 20 ml. ethyl acetate is acidified with etheral oxalic acid. The product which precipitates is filtered off and recrystallized from methanol/acetone to yield 1-[2-(1-adamantyl)-2-(2,4-dichlorobenzyloxy)ethyl]imidazole oxalate, decomp. 203.5°-205.5° C.

In similar manner, all compounds of Formula (I) in base form can be converted to the antimicrobial acid addition salts by treatment in the conventional manner with the appropriate acid.

EXAMPLE 15

A suspension of 1 g. of 1-[2-(1-adamantyl)-2-(3,4-dichlorophenylthio)ethyl]imidazole nitrate in 100 ml. of dichloromethane is treated with excess aqueous potassium carbonate until a pH of about 11 is obtained. Thereafter, the suspension is shaken until a solution is obtained. The organic phase is then separated, washed with water, dried over magnesium sulfate and evaporated to dryness to yield 1-[2-(1-adamantyl)-2-(3,4-dichlorophenylthio)ethyl]imidazole.

In like manner, the free base form of any 1-[2-(1-adamantyl)-2-(R-thio(oxy)ethyl]imidazole antimicrobial acid addition salt is obtained by treatment of the salt with an alkali such as potassium carbonate, sodium carbonate or sodium or potassium hydroxide.

EXAMPLE 16

The following example illustrates the preparation of representative formulations containing an active compound, such as a salt of 1-[2-(1-adamantyl)-2-(n-heptylthio)ethyl]imidazole, which may be used for controlling fungi, bacteria and protozoa.

| A. Topical Formulation | grams |
|---|---|
| Active compound | 0.2 – 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

| B. I.V. Formulation | |
|---|---|
| Active compound | 0.5 g. |
| Propylene glycol | 20 g. |
| Polyethylene glycol 400 | 20 g. |
| Tween 80 | 1 g. |
| 0.9% Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| C. Oral Formulation | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

What is claimed is:

1. A compound of the formula:

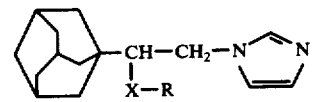

wherein R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl and wherein lower alkyl has 1 to 4 carbon atoms, alkyl has 1 to 12 carbon atoms and cycloalkyl has 5 to 7 carbon atoms; X is oxygen or sulfur with the proviso that X is not oxygen when R is phenyl or substituted phenyl; and the antimicrobial acid addition salts thereof.

2. A compound of claim 1 wherein X is oxygen.
3. A compound of claim 1 wherein X is sulfur.
4. A compound of claim 1 wherein R is alkyl.
5. The compound of claim 4 which is 1-[2-(1-adamantyl)-2-(methoxy)ethyl]imidazole and the antimicrobial acid addition salts thereof.
6. The compound of claim 4 which is 1-[2-(1-adamantyl)-2-(n-hexyloxy)ethyl]imidazole and the antimicrobial acid addition salts thereof.
7. The compound of claim 4 which is 1-[2-(1-adamantyl)-2-(n-dodecyloxy)ethyl]imidazole and the antimicrobial acid addition salts thereof.
8. The compound of claim 4 which is 1-[2-(1-adamantyl)-2-(ethylthio)ethyl]imidazole and the antimicrobial acid addition salts thereof.
9. The compound of claim 4 which is 1-[2-(1-adamantyl)-2-(heptylthio)ethyl]imidazole and the antimicrobial acid addition salts thereof.
10. The compound of claim 4 which is 1-[2-(1-adamantyl)-2-(n-dodecylthio)ethyl]imidazole and the antimicrobial acid addition salts thereof.
11. A compound of claim 1 wherein R is halo substituted benzyl or halo substituted phenyl.
12. A compound of claim 11 wherein R is chloro substituted benzyl or chloro substituted phenyl.
13. A compound of claim 12 wherein the chloro substitution in R is 4-chloro, 2,4-dichloro or 3,4-dichloro.
14. The compound of claim 13 which is 1-[2-(1-adamantyl)-2-(4-chlorobenzyloxy)ethyl]imidazole and the antimicrobial acid addition salts thereof.

15. The compound of claim 13 which is 1-[2(1-adamantyl)-2-(2,4-dichlorobenzyloxy)ethyl]imidazole and the antimicrobial acid addition salts thereof.

16. The compound of claim 13 which is 1-[2-(1-adamantyl)-2-(3,4-dichlorobenzyloxy)ethyl]imidazole and the antimicrobial acid addition salts thereof.

17. The compound of claim 13 which is 1-[2-(1-adamantyl)-2-(4, -chlorophenylthio)ethyl]imidazole and the antimicrobial acid addition salts thereof.

18. The compound of claim 13 which is 1-[2-(1-adamantyl)-2-(2,4-dichlorophenylthio)ethyl]imidazole and the antimicrobial acid addition salts thereof.

19. The compound of claim 13 which is 1-[2-(1-adamantyl)-2-(3,4-dichlorophenylthio)ethyl]imidazole and the antimicrobial acid addition salts thereof.

20. The compound of claim 13 which is 1-[2-(1-adamantyl)-2-(4-chlorobenzylthio)ethyl]imidazole and the antimicrobial acid addition salts thereof.

21. The compound of claim 13 which is 1-[2-(1-adamantyl)-2-(2,4-dichlorobenzylthio)ethyl]imidazole and the antimicrobial acid addition salts thereof.

22. The compound of claim 13 which is 1-[2-(1-adamantyl)-2-(3,4-dichlorobenzylthio)ethyl]imidazole and the antimicrobial acid addition salts thereof.

23. A composition useful for inhibiting the growth of fungi, bacteria or protozoa which comprises an effective amount of a compound of the formula

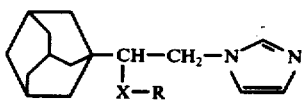

(I)

wherein R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl and wherein lower alkyl has 1 to 4 carbon atoms, alkyl has 1 to 12 carbon atoms and cycloalkyl has 5 to 7 carbon atoms; X is oxygen or sulfur with the provisio that X is not oxygen when R is phenyl and substituted phenyl; or an antimicrobial acid addition salt thereof in admixture with a suitable carrier.

24. A composition of claim 23 for pharmaceutical use wherein the carrier is a pharmaceutically acceptable, non-toxic carrier.

25. A composition of claim 24 for topical administration wherein the compound of Formula (I) is present in an amount ranging between 0.1 and 10.0 weight percent of the composition.

26. A method of inhibiting the growth of fungi, bacteria or protozoa which comprises applying to a host object containing or subject to attack by fungi, bacteria or protozoa an effective amount of a compound of the formula

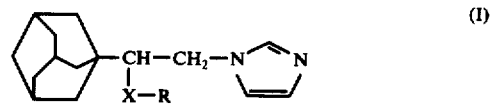

(I)

wherein R is alkyl, cycloalkyl, cycloalkyl lower alkyl, phenyl or phenyl lower alkyl, said phenyl and phenyl lower alkyl optionally substituted on the phenyl ring with one or more substituents independently selected from the group consisting of halo, lower alkyl and trifluoromethyl and wherein lower alkyl has 1 to 4 carbon atoms, alkyl has 1 to 12 carbon atoms and cycloalkyl has 5 to 7 carbon atoms; X is oxygen or sulfur with the proviso that X is not oxygen when R is phenyl or substituted phenyl; or an antimicrobial acid addition salt thereof or a composition containing same as an active ingredient.

27. The method of claim 26 wherein the compound of Formula (I) is administered topically.

28. The method of claim 26 wherein the compound of Formula (I) is administered orally or parenterally.

* * * * *